US012357198B2

(12) United States Patent
Ledet et al.

(10) Patent No.: US 12,357,198 B2
(45) Date of Patent: Jul. 15, 2025

(54) SYSTEM FOR DETERMINING A FORCE BEING GENERATED BY A PATIENT

(71) Applicant: Jenkins NeuroSpine LLC, New York, NY (US)

(72) Inventors: Eric Howard Ledet, Schenectady, NY (US); Laura Jean Bentivegna, Lawrenceville, NJ (US); Christian Bossio, Troy, NY (US); Benjamin James Liddle, Troy, NY (US); Arthur L. Jenkins, III, New York, NY (US)

(73) Assignee: Jenkins Neurospine LLC, Old Greenwich, CT (US)

( * ) Notice: Subject to any disclaimer, the term of this patent is extended or adjusted under 35 U.S.C. 154(b) by 688 days.

(21) Appl. No.: 16/859,889

(22) Filed: Apr. 27, 2020

(65) Prior Publication Data
US 2020/0345277 A1    Nov. 5, 2020

Related U.S. Application Data

(60) Provisional application No. 62/838,693, filed on Apr. 25, 2019.

(51) Int. Cl.
*A61B 5/11*    (2006.01)
*A61B 5/00*    (2006.01)
(Continued)

(52) U.S. Cl.
CPC .......... *A61B 5/1124* (2013.01); *A61B 5/6891* (2013.01); *A61B 5/743* (2013.01);
(Continued)

(58) Field of Classification Search
None
See application file for complete search history.

(56) References Cited

U.S. PATENT DOCUMENTS 3,465,592 A  *  9/1969  Perrine .............. A63B 21/4047
                                              482/5
4,979,733 A  *  12/1990  Prud'Hon ............ A63B 21/153
                                              482/901
(Continued)

FOREIGN PATENT DOCUMENTS

GB          2562486 A   *  11/2018  ........... A63B 21/005
WO    WO-2009143808 A1  *  12/2009  .......... A63B 21/0058

OTHER PUBLICATIONS

English machine translation of WO 2009143808 A1, patents.google.com, 7 pages, printed on Jan. 5, 2022 (Year: 2022).*

*Primary Examiner* — Matthew Kremer
(74) *Attorney, Agent, or Firm* — Welsh IP Law LLC

(57) ABSTRACT

A system and method for determining a patient force during a motion includes a tether adapted to be biased during a motion so that a tension force is applied. The tether is connected a motor and generates a tether force about the motor. The system controls the motor by generating a motor torque in a direction opposite the tether force. A recording module stores the motor torque at a plurality of intervals during the motion and a position of the tether. A display module generates a plot of a position of the patient versus a force generated by the patient. The position of the patient corresponds to the cumulative rotation of the shaft in the first direction about the axis of rotation of the shaft at each of the intervals. The force generated by the patient corresponds to the amount of motor torque at each of the intervals.

23 Claims, 11 Drawing Sheets

(51) Int. Cl.
 *A63B 21/00* (2006.01)
 *A63B 21/005* (2006.01)
 *A61B 90/00* (2016.01)
(52) U.S. Cl.
 CPC ........ *A63B 21/0058* (2013.01); *A63B 21/151* (2013.01); *A61B 2090/066* (2016.02); *A61B 2560/0475* (2013.01)

(56) References Cited

U.S. PATENT DOCUMENTS

| | | | | |
|---|---|---|---|---|
| 5,125,649 | A * | 6/1992 | Fuller | A63B 23/1209 482/106 |
| 5,186,695 | A | 2/1993 | Mangseth et al. | |
| 5,395,296 | A * | 3/1995 | Webster | A63B 21/04 482/130 |
| 5,800,310 | A * | 9/1998 | Jones | A63B 21/4035 482/901 |
| 10,286,253 | B1 | 5/2019 | Johnson | |
| 2004/0243025 | A1* | 12/2004 | Peles | A61H 1/0277 601/5 |
| 2005/0239600 | A1* | 10/2005 | Liang | A63B 21/00076 482/8 |
| 2008/0248926 | A1* | 10/2008 | Cole | A63B 21/0628 482/5 |
| 2014/0038777 | A1* | 2/2014 | Bird | A63B 23/03525 482/5 |
| 2017/0312582 | A1* | 11/2017 | Root, Jr. | A63B 24/0087 |

* cited by examiner

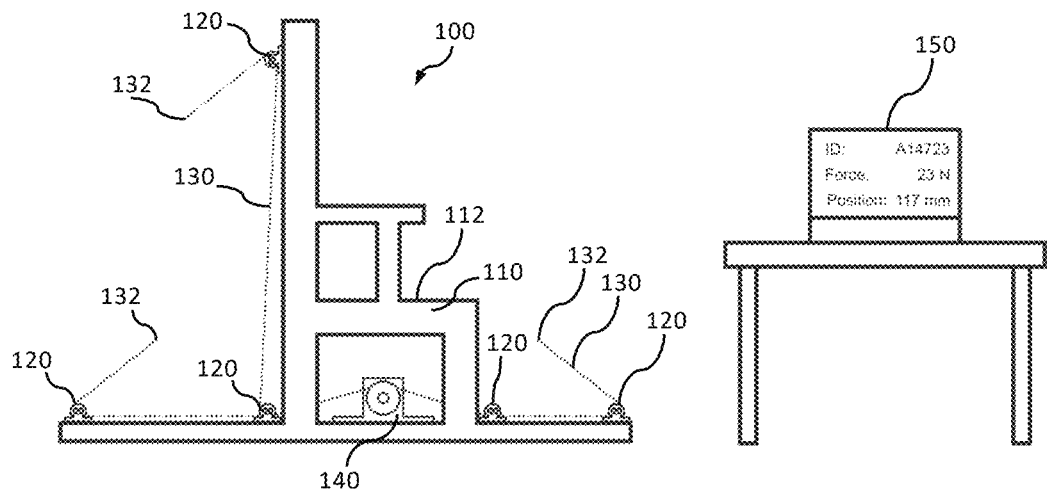
FIG. 1A
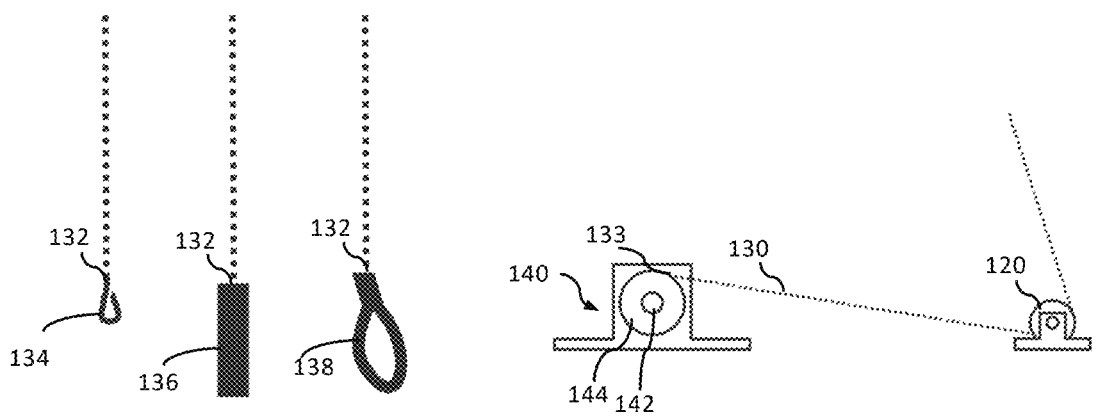
FIG. 1B
FIG. 1C

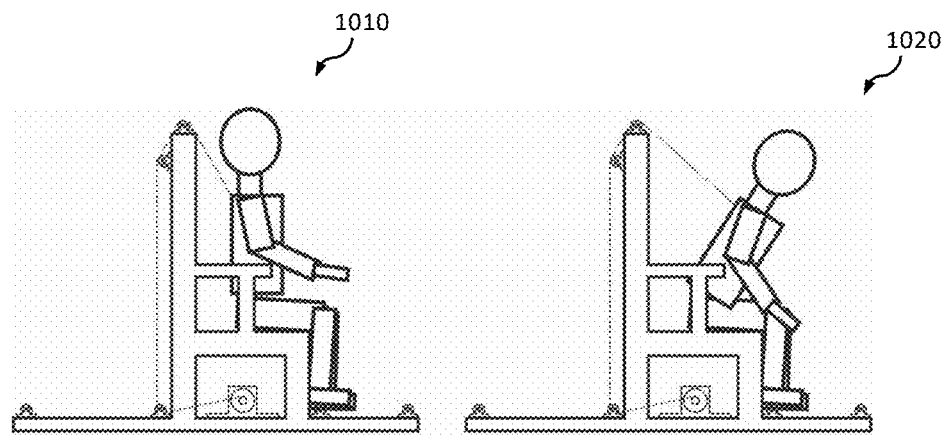
FIG. 10A
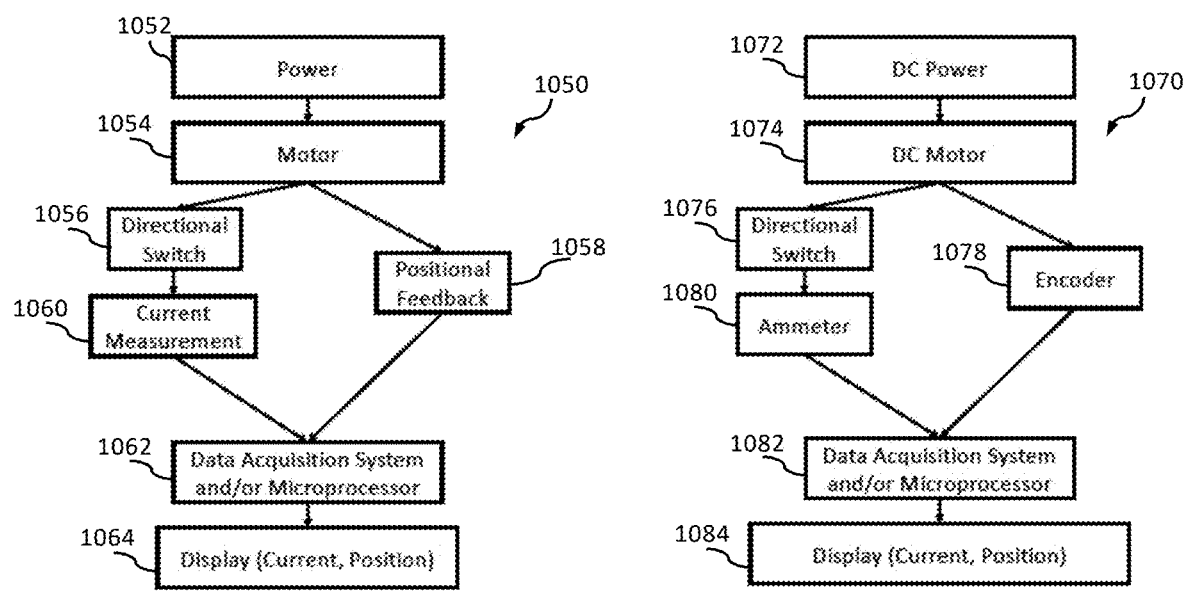
FIG. 10B
FIG. 10C

SYSTEM FOR DETERMINING A FORCE BEING GENERATED BY A PATIENT

TECHNICAL FIELD

The present invention relates to a system for determining a force being generated by a patient. More specifically, the present invention relates to a system and method for measuring range of motion of a patient and for measuring force or torque transmitted by the patient throughout the entire range of motion.

BACKGROUND

Musculoskeletal disorders, such as osteoporosis, arthritis, and neck or back pain affect approximately 126.6 million Americans, or about 1 in 2 adults. Certain diseases afflict a specific demographic whereas other conditions can affect anyone. As an example, in people over the age of 50, osteoporosis effects on average 1 in 2 women compared to 1 in 4 men. Some jobs or industries have working conditions where an employee is more prone to getting injured. Arthritis is a condition that affects people as they age, resulting in 51.8 million American adults over the age of 65 being afflicted. In general, musculoskeletal conditions can affect anyone, regardless of age, and limits a person's daily life and activities to some extent.

Currently, diagnosis of a musculoskeletal problem involves a physical exam. Most often, a person will only see a doctor once they are experiencing pain or noticing a decrease in function. A physician should assess a person with a physical exam and look for pain, redness, swelling, and muscle weakness or atrophy. Based on this initial exam, the doctor should then recommend a treatment plan, which could involve doing more tests or referring to see another professional, such as a surgeon or physical therapist.

When initially assessing a patient with a musculoskeletal condition, especially in physical therapy, a doctor or therapist will often take a medical history and ask about symptoms such as pain, stiffness, fatigue, and joint instability. During the exam, the practitioner may want to assess the force a muscle group can produce. This involves the practitioner having the patient execute some motions with the joint or muscle group. Based on what the patient can do, a rating on a scale of 0 to 5, 0 being the worst and 5 being the best, is often assigned. A practitioner may also test a person's range of motion. He will do this by assessing the active range of motion, when the patient moves the joint, a passive range of motion, and when the practitioner moves the joint. If a practitioner wants a quantitative number for a joint's range of motion, he may use a device called a goniometer. This goniometer is a device with two arms, one stationary and one moveable, that are positioned at points around a joint, with a scale like that of a protractor. When the device is used, it can measure the angles of motion a joint can go through.

While range of motion can be measured quantitatively, not all practitioners measure joint angles. Therefore, assessments and measurements of a musculoskeletal disorder are very qualitative and highly subjective. There is a need for a system that can quantitatively measure the range of motion of patient, including the range of motion of a joint, and the subsequent force generated by the patient across the range of motion. This will allow practitioners to precisely track a patient's progress to objectively determine if a patient is improving or getting worse, and subsequently if the treatment plan is working or not.

In addition, there is a need for a system which could add uniformity to how musculoskeletal disorders are diagnosed. Musculoskeletal disorders can be treated by different doctors (e.g. general practitioner, orthotist, physical therapist, or neurologist). Having a quantitative measure for assessing a patient would give quantitative numbers and data points on a patient's progress. This is essential since different doctors pay more attention to different parameters, but any data on a patient will help to make an informed decision on their path of treatment. For example, a neurosurgeon would more likely help to improve a patient's muscle function rather than their range of motion. A physical therapist is looking to get a patient back to daily activities, which most often meanings improving range of motion and then building up muscle. A general practitioner may look to simply cure a person's ailment and then recommend physical therapy and have that be it. Having uniform information of progress over an extended period of time helps track a patient's progress, see what treatments have or have not worked and how the patient is improving.

SUMMARY

The needs set for the herein as well as further and other needs and advantages are addressed by the present teachings, which illustrate solutions and advantages described below.

The present invention resides in one embodiment in a system for determining a force being generated by a patient during a range of motion. The system includes a tether having a first end and a second end. The first end of the tether is adapted to be biased by the patient during a motion so that a tension force is applied along the tether during the motion. The system includes a motor fixed relative to a frame. The motor comprises a shaft having an axis of rotation. The tether is connected to the shaft so that when the tension force is applied along the tether during the motion the tether generates a torque about the shaft in a first direction about the axis of rotation of the shaft. The system includes a control module in communication with the motor and adapted to control the motor to generate a motor torque in a second direction about the axis of rotation of the shaft, the second direction being opposite the first direction, when the tension force is applied along the tether during the motion. The system further includes a recording module for storing the motor torque at a plurality of intervals during the motion and for storing a cumulative rotation of the shaft at each of the intervals. The system further includes a display module for generating a plot of a position of the patient versus a force generated by the patient. The position of the patient corresponds to the cumulative rotation of the shaft in the first direction about the axis of rotation of the shaft at each of the intervals. The force generated by the patient corresponds to the amount of motor torque at each of the intervals.

In yet another embodiment of the present invention, the control module varies the motor torque in the second direction in proportion to the torque applied by the tether during the motion so that the shaft of the motor has a constant rotational velocity in the first direction about the axis of rotation of the shaft.

In yet another embodiment of the present invention, the control module varies an electrical current supplied to the motor to cause the proportional variation in motor torque in the second direction in proportion to the torque applied by the tether during the motion.

In yet another embodiment of the present invention, the frame comprises a chair having a surface configured to support a portion of the patient.

In yet another embodiment of the present invention, the system comprises a pulley configured to support the tether during the motion.

In yet another embodiment of the present invention, the system comprises a gear being fixed on the shaft of the motor, wherein the tether is connected to the shaft via the gear.

In yet a further embodiment of the present invention, the motor is selectively fixed to the frame via a track and the motor has an unlock mode and a lock mode, wherein in the unlock mode the motor is translatable along a length of the track and wherein in the lock mode the motor is fixed relative to the track.

In yet a further embodiment the system comprises an interface module in communication with the control module, the interface module is adapted to receive an indication regarding the type of motion and transmit the instruction to the control module so as to maintain a constant rotational velocity in the first direction about the axis of rotation of the shaft appropriate for the type of motion.

In yet another embodiment of the present invention, the system comprises a storage module for storing a plot associated with a patient identifier.

In yet a further embodiment of the present invention, the system comprises a module for generating a display simultaneously showing a first plot a position of the patient versus a force generated by the patient at a first time and a second plot of a position of the patient versus a force generated by the patient at a second time different than the first time. In yet a further embodiment the plot is shown on a display unit.

In yet another embodiment of the present invention, the system comprises an encoder. The encoder is configured to monitor the cumulative rotation of the shaft and determine a displacement of the tether, wherein the displacement correlates to the range of motion.

The present invention resides in yet a further aspect in a method for determining a force being generated by a patient during a range of motion. The method comprises the step of providing a tether having a first end and a second end, the first end of the tether adapted to be biased by the patient during a motion so that a tension force is applied along the tether during the motion. The method further includes the step of providing a motor fixed relative to a frame, the motor comprising a shaft having an axis of rotation, the tether being connected to the shaft so that when the tension force is applied along the tether during the motion the tether generates a torque about the shaft in a first direction about the axis of rotation of the shaft. The method further includes the step of controlling the motor to generate a motor torque in a second direction about the axis of rotation of the shaft, the second direction being opposite the first direction, when the tension force is applied along the tether during the motion. The method further includes the step of storing the motor torque at a plurality of intervals during the motion and for storing a cumulative rotation of the shaft at each of the intervals. The method further includes the step of generating a plot of a position of the patient versus a force generated by the patient. The position of the patient corresponds to the cumulative rotation of the shaft in the first direction about the axis of rotation of the shaft at each of the intervals. The force generated by the patient corresponds to the amount of motor torque at each of the intervals.

In yet another embodiment of the method, the controlling step varies the motor torque in the second direction in proportion to the torque applied by the tether during the motion so that the shaft of the motor has a constant rotational velocity in the first direction about the axis of rotation of the shaft.

In yet another embodiment, the control step comprises varying an electrical current supplied to the motor to cause the proportional variation in motor torque in the second direction in proportion to the torque applied by the tether during the motion.

In yet a further embodiment, the method further comprises the steps of providing a gear fixed on the shaft of the motor and connecting the tether to the shaft via the gear.

In yet a further embodiment, the method further comprises the steps of receiving an indication regarding the type of motion and transmitting the instruction to the control module so as to maintain a constant rotational velocity in the first direction about the axis of rotation of the shaft appropriate for the type of motion. In yet a further embodiment, the invention includes the step of storing a plot associated with a patient identifier.

In yet a further embodiment of the present invention, the method includes the step of generating a display simultaneously showing a first plot a position of the patient versus a force generated by the patient at a first time and a second plot of a position of the patient versus a force generated by the patient at a second time different than the first time.

Other teachings of the system and method are described in detail below and are also part of the present teachings.

For a better understanding of the present teachings, together with other and further aspects thereof, reference is made to the accompanying drawings and detailed description, and its scope will be pointed out in the appended claims.

BRIEF DESCRIPTION OF THE DRAWINGS

FIG. 1A illustrates a system for determining a force being generated by a patient during a range of motion FIG. 1B illustrates different attachments for use with the system illustrated in FIG. 1A.

FIG. 1C illustrates a portion of the system shown in FIG. 1A.

FIG. 10A illustrates an embodiment of the present invention during which the force generated by a patient is measured during bending of the torso while the patient is sitting in a chair.

FIG. 10B illustrates a flow chart for in accordance with operation of one embodiment of the present invention.

FIG. 10C illustrates a flow chart for in accordance with operation of one embodiment of the present invention.

DETAILED DESCRIPTION

Figure 2:
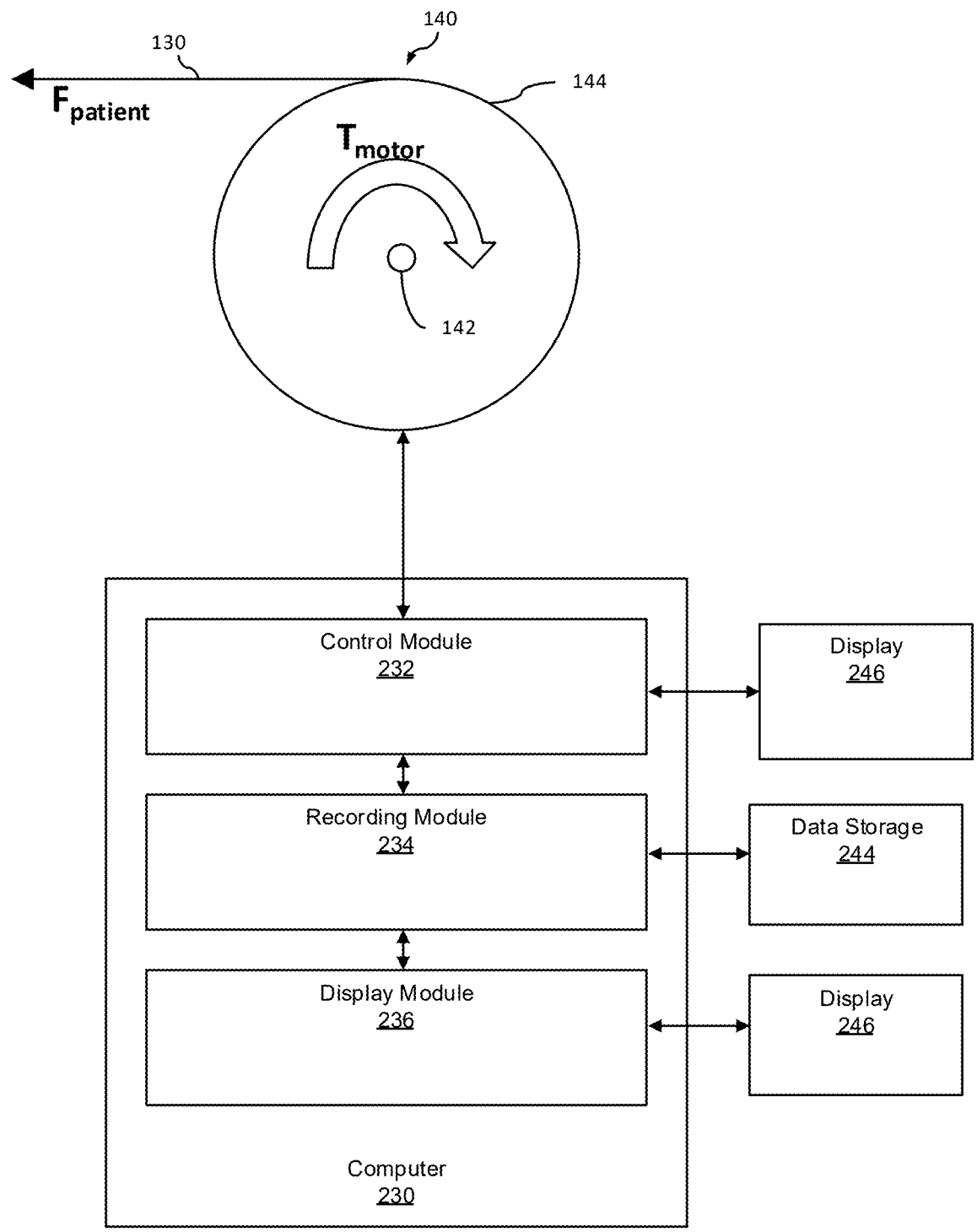
FIG. 2 is a diagram further illustrating the system shown in FIG. 1A.

The present teachings are described more fully hereinafter with reference to the accompanying drawings. The following description is presented for illustrative purposes only and the present teachings should not be limited to these embodiments. Any computer configuration and architecture satisfying the speed and interface requirements herein described may be suitable for implementing the system and method of the present embodiments.

In compliance with the statute, the present teachings have been described in language more or less specific as to structural and methodical features. It is to be understood, however, that the present teachings are not limited to the specific features shown and described, since the systems and methods herein disclosed comprise preferred forms of putting the present teachings into effect.

For purposes of explanation and not limitation, specific details are set forth such as particular architectures, interfaces, techniques, etc. in order to provide a thorough understanding. In other instances, detailed descriptions of well-known devices, circuits, and methods are omitted so as not to obscure the description with unnecessary detail.

Generally, all terms used in the claims are to be interpreted according to their ordinary meaning in the technical field, unless explicitly defined otherwise herein. All references to a/an/the element, apparatus, component, means, step, etc. are to be interpreted openly as referring to at least one instance of the element, apparatus, component, means, step, etc., unless explicitly stated otherwise. The steps of any method disclosed herein do not have to be performed in the exact order disclosed, unless explicitly stated. The use of "first", "second," etc. for different features/components of the present disclosure are only intended to distinguish the features/components from other similar features/components and not to impart any order or hierarchy to the features/components.

In reference to FIGS. 1A, 1B, 10, and 2 a system 100 in accordance with one embodiment of the present disclosure is shown. The specific embodiment is provided for the purpose of illustrating the system and is not intended to limit the present disclosure. A person of ordinary skill in the art and familiar with this disclosure will understand that different embodiments and configurations may by employed to practice the presently disclosed systems in methods.

The system 100 is employed for determining a force being generated by a patient during a range of motion. The system 100 includes a tether 130 having a first end 132 and a second end 133. The first end 132 of the tether 130 is adapted to be biased by a patient (now shown in FIGS. 1 and 2) during a motion to that a tension force is applied along the tether 130 during the motion.

In the embodiment shown in FIG. 1A, the tether 130 is formed from a wound cable that extends between the first end 132 and the second end 133. The tether 130 is substantially inelastic along its linear axis so as to facilitate a smooth transition tension force along its length during operation. A person of ordinary skill in the art and familiar with this disclosure will understand that it is possible to adjust the elasticity of the tether to enhance use by the patient, particularly to provide a smooth effect of force initiation and termination during the specific movement. In the embodiment disclosed, the tether 130 is flexible to an extent that it may be fed through on or more pulleys to redirect the tension force. A person of ordinary skill and familiar with this invention, will understand that in alternative embodiments, it is not required to feed the tether through pulleys. In other embodiments, the tether may comprise strap or webbing comprising a polymer material. In yet other embodiments, the tether may comprise a natural material such as a wound cotton line. A person of ordinary skill in the art and familiar with this disclosure will understand the many different embodiments and material types may be used as a tether.

A motor 140 is fixed to a frame 110 of the system 110. The motor 140 comprises a shaft 142 that has an axis of rotation. The tether 130 is connected to the shaft 142, either directly or through one or more intermediate pieces adapted for collecting and paying out the tether 130. The tether 130 is connected to the shaft 142 of the motor 140 so that when a tension force is applied along the tether 130 by a force generated by a patient during a motion the tether 130 generates a torque about the shaft 142 in a first direction about the axis of rotation of the shaft. In reference to FIG. 2, a cross-section of motor shaft 142 is illustrated for the purpose of showing the relative forces and direction. A person of ordinary skill in the art will understand the system shown in FIG. 2 is for illustration persons only, and that the system in accordance with the present invention may incorporate additional hardware. In reference to FIG. 2, the tension force F applied by the tether to a gear affixed to a motor shaft 142 the tether generates a torque about shaft 142 in the first direction about the axis of rotation of the shaft 142. This is in the counterclockwise direction in reference to the diagram shown in FIG. 2.

In reference to FIG. 2, a gear 144 is shown for spooling a portion of the tether 130. As the patient applies a tension force to the spool 144 via the tether 130, the spool 144 may rotate in the counterclockwise direction (as further described below), thereby paying out additional length of tether as the patient performs one or more prescribed body movements for which an assessment is sought. After the movement is completed, a length of tether can be spooled on the gear 144 by rotating the gear in the clockwise direction. In this manner, it is possible to perform subsequent assessments. It should be understood to a person of ordinary skill in the art and familiar with this disclosure that different configurations are possible. For example, in one embodiment the tether is spooled on a gear remote from the motor. In such an embodiment, the tether is fixedly wrapped around a portion of the gear to enable the motor to control the payout thereof.

In reference to FIG. 2, the motor 140 is connected with a computer 230. In the embodiment disclosed, a computer shall include any device comprising a microprocessor and capable of implements the control protocols described herein. The computer 230 includes a control module 232 operating thereon and in communication with the motor 140. The control module 232 controls operation of the motor in accordance with the present invention to measure a force generated by the patient during use of the system. In the embodiment shown in FIG. 2, the control module 232 is adapted to control the motor to generate a motor torque in a second direction about the axis of rotation of the shaft 242. In reference to FIG. 2, the second direction, illustrated by the T force T motor, is clockwise. In this manner, the torque created by the motor 140 is opposite to the torque force applied by the patient via the tether 130. As the patient performs a prescribed movement, for example an extension of the elbow, while holding a first end of the tether, the patient transmits a tension force F patient along the tether 130 to the motor 140. The control module 232 operates the motor 140 in such a manner to generate a variable force in the opposing direction. In this manner, the system 100 can control the rate at which a portion of spooled tether is payed out as the patient performs the movement. It is expected that the patient force will vary across the range of motion due to, for example, dynamic changes in the natural lever of the portion of the human body performing the movement, conscious or subconscious changes in the effort put forth by the patient, and natural phenomena related to the patient's physiology, such as strength and control. In some embodiments of the present invention, the control module 232 is adopted to vary the torque on motor 140 so that the motor pays out spooled tether at a constant velocity during the range of motion. The control module 232 includes software for determining a length of tether unspooled during the movement of the patient. In some embodiments, the position of the line is calculated based on the rate of rotation of the gear 144, or the like. In yet other embodiments, the position is determined by an encoder which physically monitors to rotation.

In further reference to FIG. 2, the system 100 includes a recording module 234 operating on the computer and in communication with the control module and the motor 140. The recording module 234 is adapted for capturing and storing the motor toque at a plurality of intervals during the motions of the patient and for storing a cumulative rotation of the shaft at each of the intervals. It should be understood that cumulative rotation of the shaft is a metric that refers to the amount of tether unspooled by the patient during the movement.

Figure 3A:
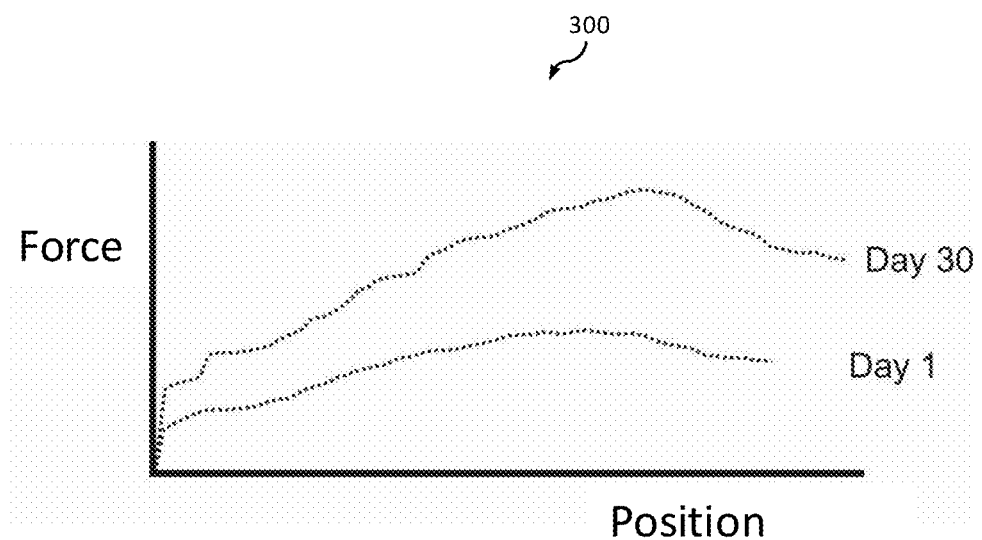
FIG. 3A is a plot shown position versus force during a movement of a patient.
Figure 3B:
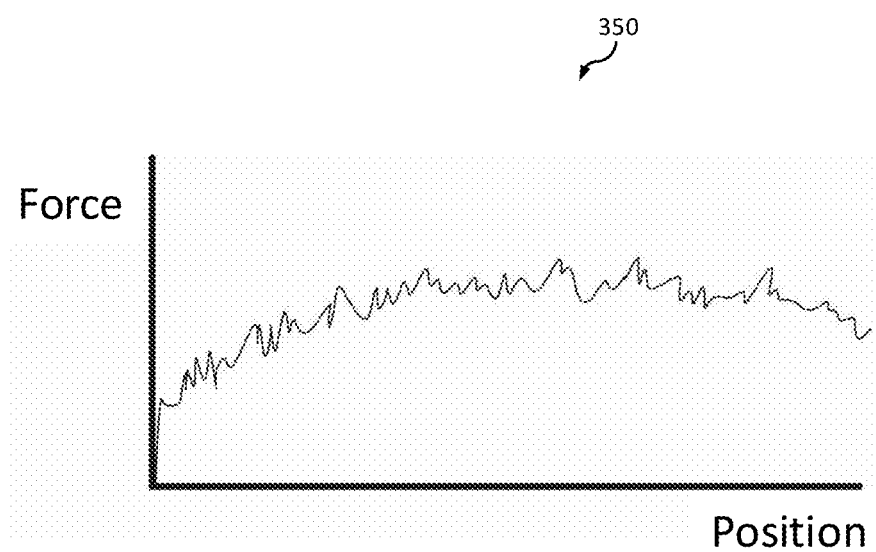
FIG. 3B is a plot shown position versus force during a movement of a patient.

In further reference to FIG. 2, the system includes a display module for generating a plot of a position of the patient versus a force generated by the patient. In some embodiments, the plot is shown on a display 246 in communication with the computer 230. An example of such a plot is shown in FIGS. 3A and 3B. In the generated plot, the position of the patient corresponds to the cumulative rotation of the shaft in the first direction about the axis of rotation of the shaft at each of the intervals. The force generated by the patient corresponds to the amount of motor torque at each of the intervals.

Figure 6A:
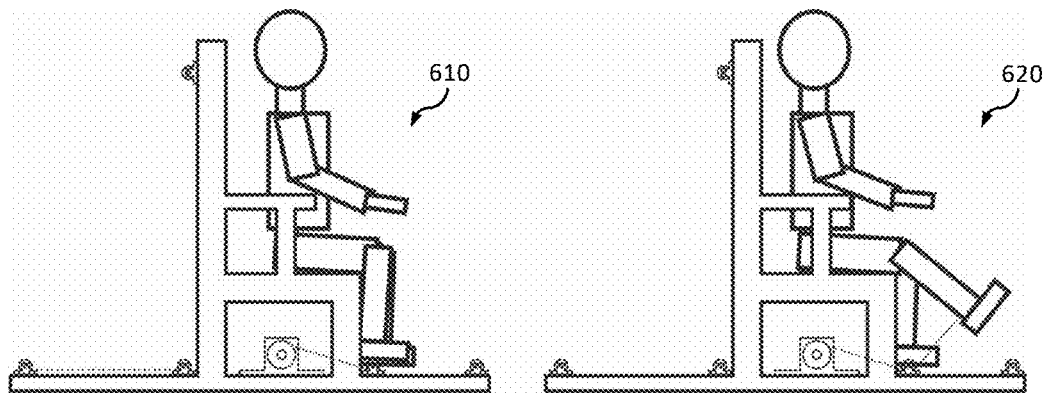
FIG. 6A illustrates one embodiment of the present invention during which the force generated by a patient is measured during the extension of the patient's knee.
Figure 6B:
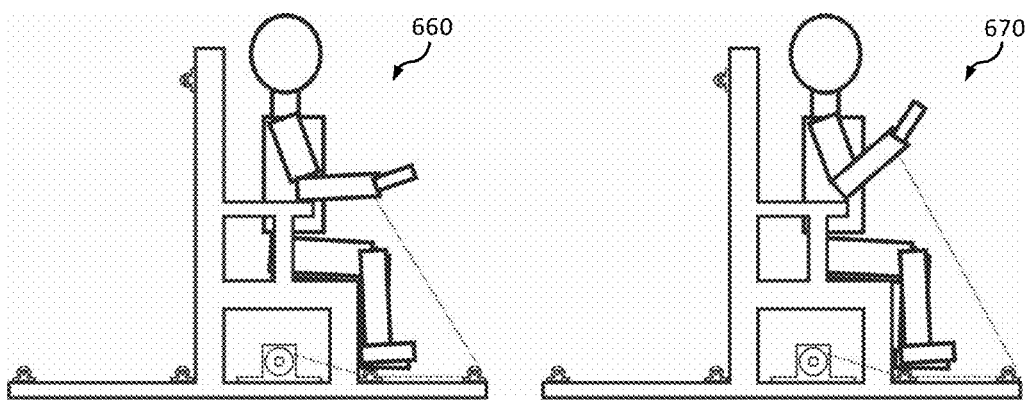
FIG. 6B illustrates one embodiment of the present invention during which the force generated by a patient is measured during the extension of the patient's elbow.

In reference to FIG. 6A, an example of a body movement of use with the present invention is disclosed. Specifically, FIGS. 6A and 6B illustrate a patient performing a seated knee extension. The first end of the tether is connected to the patient proximate to an ankle of the patient. In reference to 6A, on the left side, the patient is shown in the starting position. During the movement, the patient lifts her leg by rotating at the knee, thereby introducing a tension force into the tether. On the right side, the patient is shown with the leg in the fully extended position. During the course of the movement, the control module maintains a constant velocity unspooling of the tether, while the recording module measures the force introduced by the patient at different intervals during the movement and the position of the patient. In the embodiment disclosed, the recording module captures a data point at 5 millisecond intervals. In this manner, the system captures sufficient data to provide a near continuous illustration of the force generated by the patient throughout the motion. It should be understood, however, to a person of skill in the art and familiar with the disclosure the period of sampling may be varied.

In reference to FIG. 3A chart illustrating the position of the patient's leg shown in FIG. 6A versus the force exerted by the patient is shown. The first plot is identified as day 1 and indicates the data captured by a movement performed by the patient during the first day of a recovery period. The second plot is identified as day 30 and indicates the data captured by the same movement performed by the patient during the thirtieth day of a recovery period. In reference to each of the plots, the x-axis is indicative of the position of the leg during the extension and the y-axis is indicative of the force generated by the leg. As shown in each of the plots, the force increases gradually throughout the movement and then subsides in the last third of the movement.

The inventors have discovered that by employing such plots of exercises performed by patients it is possible to perform both latitudinal studies, wherein a patient is compared to a sample of similar patients, and longitudinal studies, wherein a patient is compared at two or more different times. In this manner, it is possible to provide an objective quantitative assessment of a patient's strength and range of motion in an exercise. This data is particularly relevant to a medical professional in assessing the status of a patient or the improvement or deterioration of a patient, or the response of the patient to a medical intervention. For example, the data provides a therapist with an objective data as to whether a specific therapy provided during a period of time is effective for the patient. Likewise, insurance companies can use this data to adequately assess a patient's need for certain medical care that is covered by an insurance policy owned by the patient. In yet other embodiments of the present invention, the objective data can be used to assess the veracity of a patient's injury. This may be particularly useful to minimize fraudulent claims or unscrupulous patients that are seeking faking an injury to obtain narcotics. This system will help the practitioner better identify this fraud and potentially direct a patient to an appropriate substance abuse therapy.

It should be understood to a person of ordinary skill in the art and familiar with this invention, that the present invention is not limited in this regard and that it may be used for other purposes. In reference to FIG. 3B, a plot of position versus force of patient is shown that was recorded during a tested movement. The data line exhibits a wave as the position extends indicating that the force subject to variations along the movement. This is excepted as the force generate by the body typically fluctuates within a range during a particular limit. In some embodiments of the present invention, this variation can be observed to aid practitioners in identifying the early onset of a condition or disease in a patient. For example, a patient with Parkinson's disease would exhibit greater variation in force across the motion of the exercise. A doctor, for example, may observe this variation in the data of a patient and recommend further testing in diagnosis. In yet other embodiments of the present invention, software executing on the system analyzes the data and determines noise factor based on the force variation. The system then compares the determined noise factor with known data sets to determine whether the patient falls within one or more subsets related to a particular category that requires further assessment.

In reference to FIG. 1, the motor 140 can be a DC motor, servo motor, or other type of electrical motor. The frame can be generally flat 112 and mounted to a floor or wall or it can be in other shapes such as the shape of a chair. The tether 130 may be a cable or rope or other material capable of sustaining tension. The tether is attached to the motor shaft in a way that as the motor turns the tether is either wound in or wound out depending on the direction of motion of the motor. The tether may be attached directly the shaft of the motor or it may be attached via a pulley which is mounted to the shaft. The motor is mounted to the frame and may be fixed in place or may be slidable along the frame or repositionable at different locations on the frame.

One end of the tether attaches to the motor or motor-mounted pulley while the other end of the tether interfaces with the patient. The patient-end of the tether interfaces with the patient to allow the patient to pull on the tether as they flex or extend at least one joint of their body. As the joint is flexed or extended, it causes tension in the tether and the tensile force then causes a torque about the shaft of the motor. In reference to FIG. 1B, the patient-end 132 of the tether may be comprised of a grip or handle for holding in the hand or it may be comprised of a strap or belt 138 or closure for wrapping around a body part or it may be comprised of a belt, corset, garment, headband, or hat for interfacing with the torso or head. It may also comprise a carabiner 134. As the joint in the extremity, torso, or neck is flexed or extended, the tether is put into tension and the tension transmitted to a torque about the motor.

Figure 7A:
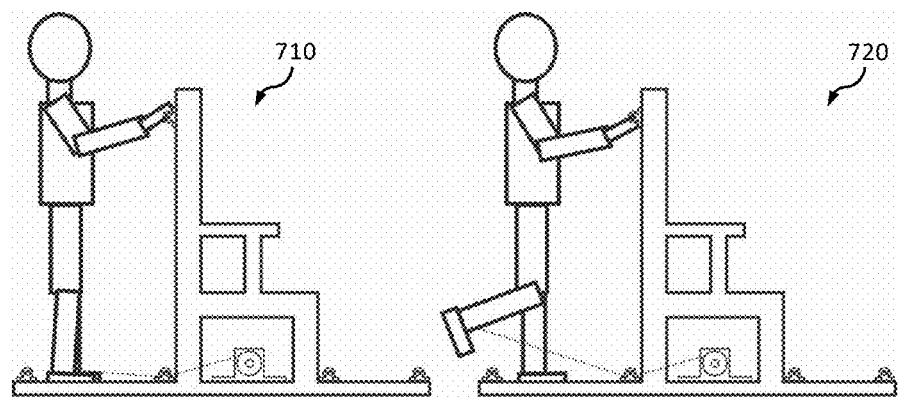
FIG. 7A illustrates another embodiment of the present invention during which the force generated by a patient is measured during the extension of the patient's knee.
Figure 7B:
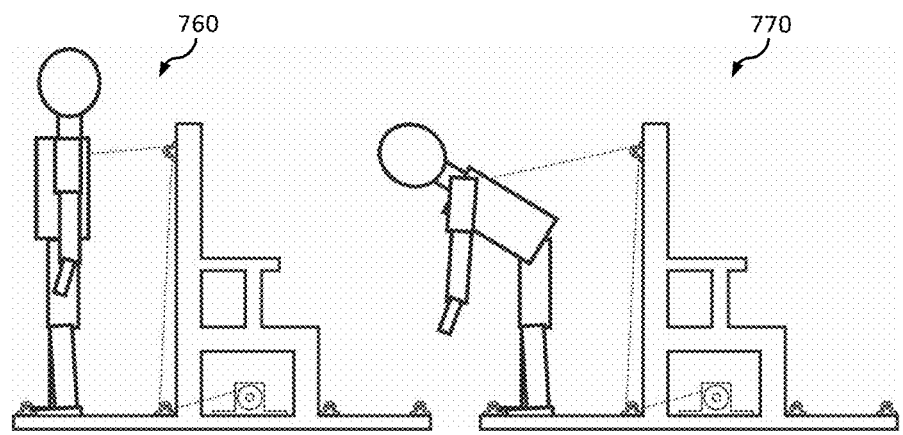
FIG. 7B illustrates another embodiment of the present invention during which the force generated by a patient is measured during while the patient is bending forward.
Figure 8A:
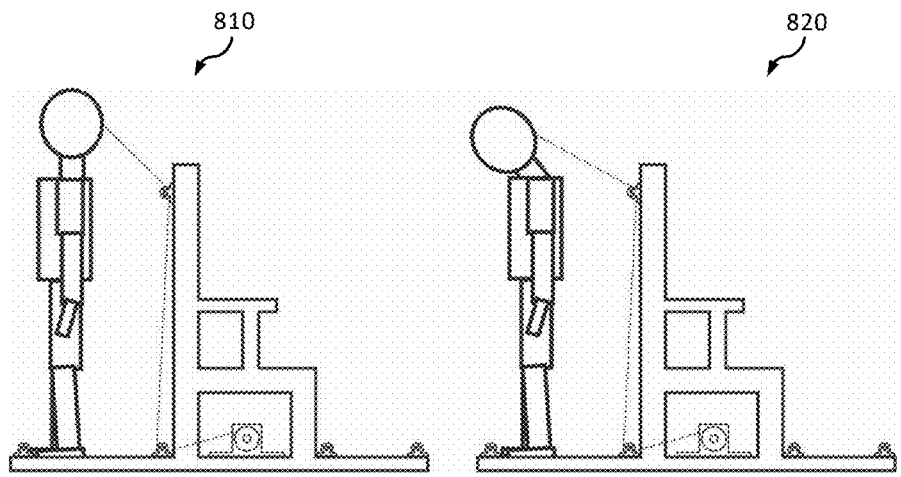
FIG. 8A illustrates an embodiment of the present invention during which the force generated by a patient is measured during bending of the neck.
Figure 9A:
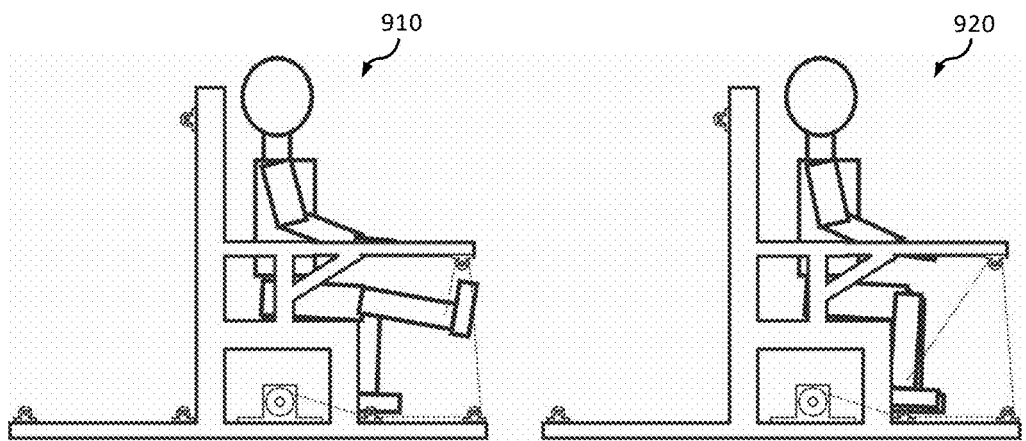
FIG. 9A illustrates an alternative embodiment of the present invention in which the force generated by the patient is measured during retracting of the knee.
Figure 9B:
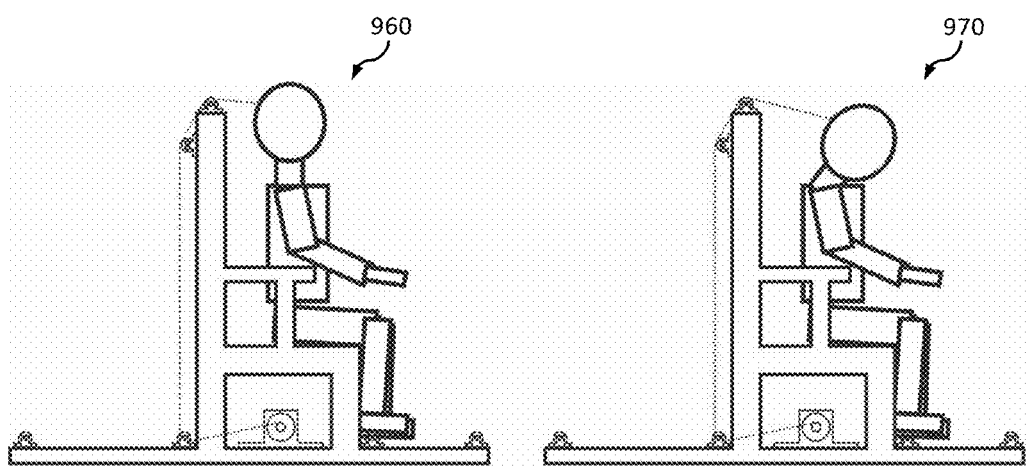
FIG. 9B illustrates an embodiment of the present invention during which the force generated by a patient is measured during bending of the neck while the patient is sitting in a chair.

The system can be used for flexion, extension, lateral bending, torsion, internal rotation, external rotation, supination, pronation, inversion, eversion, and motions about joints in other directions. Different examples of exercises are shown in FIGS. 6A, 6B, 7A, 7B, 8A, 9A, 9B, and 10A. In reference to FIG. 6A, the system is measuring force of the patient during a seated elbow extension. In FIG. 6B, the system is measuring force of the patient during a seated knee extension. In FIG. 7A, the system is measuring force of the patient during a standing knee bend. In FIG. 7B, the system is measuring force of the patient during a bend at the patient torso. In FIG. 8A, the system is measuring force of the patient during a neck movement extension. In FIG. 9A, the system is measuring force of the patient during a seated reverse knee extension. In FIG. 9B, the system is measuring force of the patient during a seated neck extension.

Figure 8B:
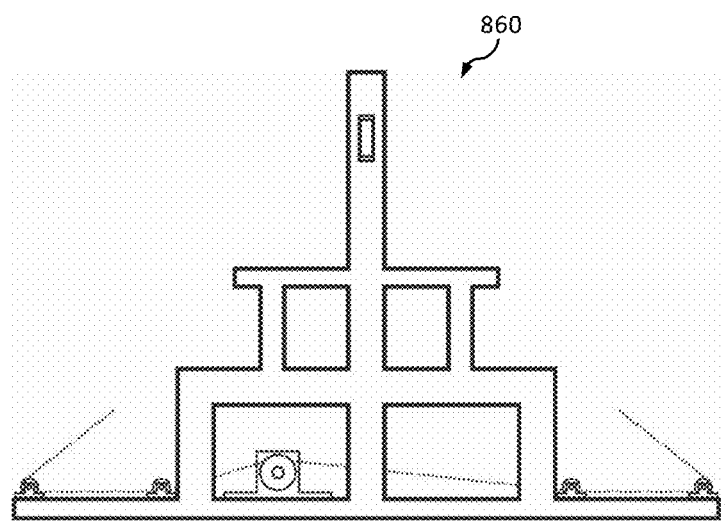
FIG. 8B illustrates an embodiment of a frame in accordance with one embodiment of the present invention.

In reference to FIG. 8B, an embodiment of a frame is shown in which the frame comprises a first and second seating surface. In reference to the FIGS, the system includes a plurality of pulleys that are optionally used to redirect the force generated by the patient to the motor. In some embodiments, the motor and the pulleys are fixed on adjustable tracks, so that the position of the motor and the pulleys can be used to accommodate different motions and different size patients. A person of ordinary skill in the art and familiar with this disclosure will understand that the position and attachment thereof of the pulleys and the motor can vary.

In some embodiments of the present invention, an electrical current sensor or other current sensing circuit may be wired to the motor and power supply circuit for the motor such that the current sensor measures the current demand of the motor. In this way, the current sensor senses the current demand of the motor. One or more of the current sensors and the motor are connected to a controller having software executing thereon and having an interface for controlling such software. In some embodiments of the present invention, the system is further connected to a database for storing data and providing an accessible library of data for access by the software. A person of skill in the art and familiar with this disclosure will understand that such a database is optional and not required to operate the system. Through use of the control circuit, the system can determine an amount of force applied to the shaft of the motor. The system can further rotate the shaft of the motor in specified increments while the shaft is under load. The system can determine, through the control circuit, the amount of rotation of the shaft thereby enabling conversion to a range of joint extension.

In alternative embodiment, a load cell or other force sensor may be placed in series with the tether such that the forces imposed on the tether are transmitted through the load cell. In this way, the load cell measures forces imposed on the tether by the joint. Alternatively, a torque cell or other torque sensor may be placed between the motor shaft and the tether or between the motor shaft and the pulley such that the torques imposed on the motor are transmitted through the torque cell. In this way, the torque cell measures torque imposed on the motor by the joint.

An encoder or other transducer which measures rotation of the motor may be attached to the motor to measure the amount of rotation of the motor.

The system is used for measuring range of motion of a joint and for measuring force or torque transmitted by that joint throughout the entire range of motion.

In some embodiments of the present invention, the user attaches the patient-end of the tether to a part of their body. For example, they may use a strap to connect the tether to their forearm. The user then flexes a joint such as the elbow and in doing so causes tension in the tether. The tension in the tether will cause a torque about the motor shaft and will have a tendency to rotate the motor shaft. However, the motor is programmed to maintain its position in spite of the tension in the tether and thus does not initially move. In order to maintain its position against the torque of the tether, the motor pulls more current from its power supply. The amount of current pulled by the motor from the power supply is indicative of the amount of torque that the motor has to overcome to maintain its position. Thus, by measuring current, the torque on the motor can be determined. Alternatively, the torque on the motor can be measured by a torque cell attached to the shaft of the motor. Alternatively, the force in the tether can be measured by a load cell placed in series with the tether.

Once the peak torque or force is measured at the starting position, the motor allows itself a small increment of motion in the direction which is being encouraged by the tether. At the new position, the motor is again programmed to maintain its new position in spite of the tension in the tether and thus does not move from the new position. In order to maintain its new position against the torque of the tether, the motor pulls more current from its power supply. The amount of current pulled by the motor from the power supply is indicative of the amount of torque that the motor has to overcome to maintain its new position. Again, by measuring current, the torque on the motor can be determined. Alternatively, the torque on the motor in the new position can be measured by a torque cell attached to the shaft of the motor. Alternatively, the force in the tether at the new position can be measured by a load cell placed in series with the tether.

Once the peak torque or force is measured in the new position, the motor allows itself another small increment of motion in the direct which is being encouraged by the tether. The process of incremental motion followed by fixed position and measurement of torque followed by incremental motion is repeated through the entire range of motion of the at least one joint in question. Using this system, the total motion can be determined by using the encoder to measure motor motion. The torque at each position is also measured by correlating the location of the motor (via the encoder) to the torque (via the current sensor). In some embodiments of the present invention, this incremental method is performed so that it appears as a constant velocity to the patient.

For example, in some embodiments, to ensure the motion occurs in a controlled manner, the control system will only allow for motion during predetermined windows of time (~100 milliseconds), otherwise it will hold the motors current position (for another ~100 milliseconds). The result will be a motion at a "constant" speed in a step-like fashion. It should be understood to a person of ordinary skill in the art and familiar with this disclosure that this time frame is presented for illustration purposes only and is not intended to limit the present invention.

Figure 4:
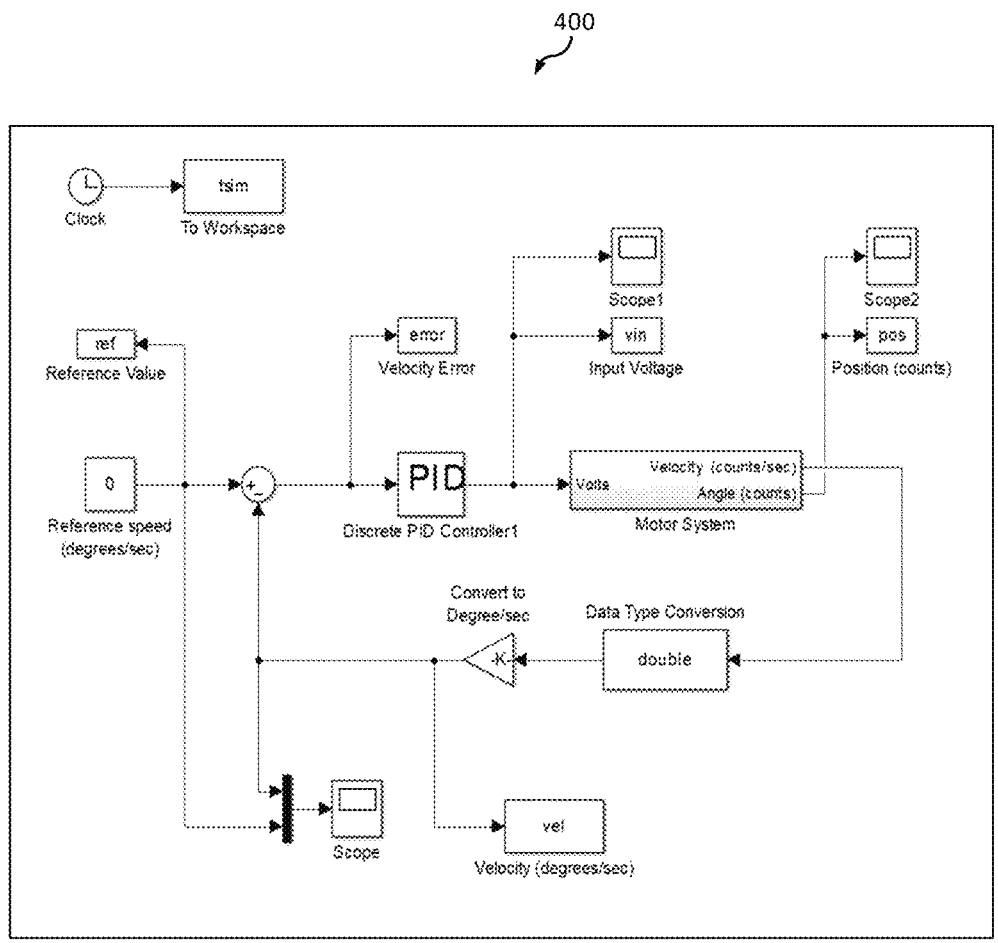
FIG. 4 is a schematic illustrating a control system in accordance with one embodiment of the present invention.

In reference to FIG. 4, a Simulink diagram is shown to illustrate the system used to regulate the rotational velocity of a DC Motor by implementing PID controls and closed feedback loop. Different values like error, input voltage, velocity and others are saved to Workspace to process.

Figure 5:
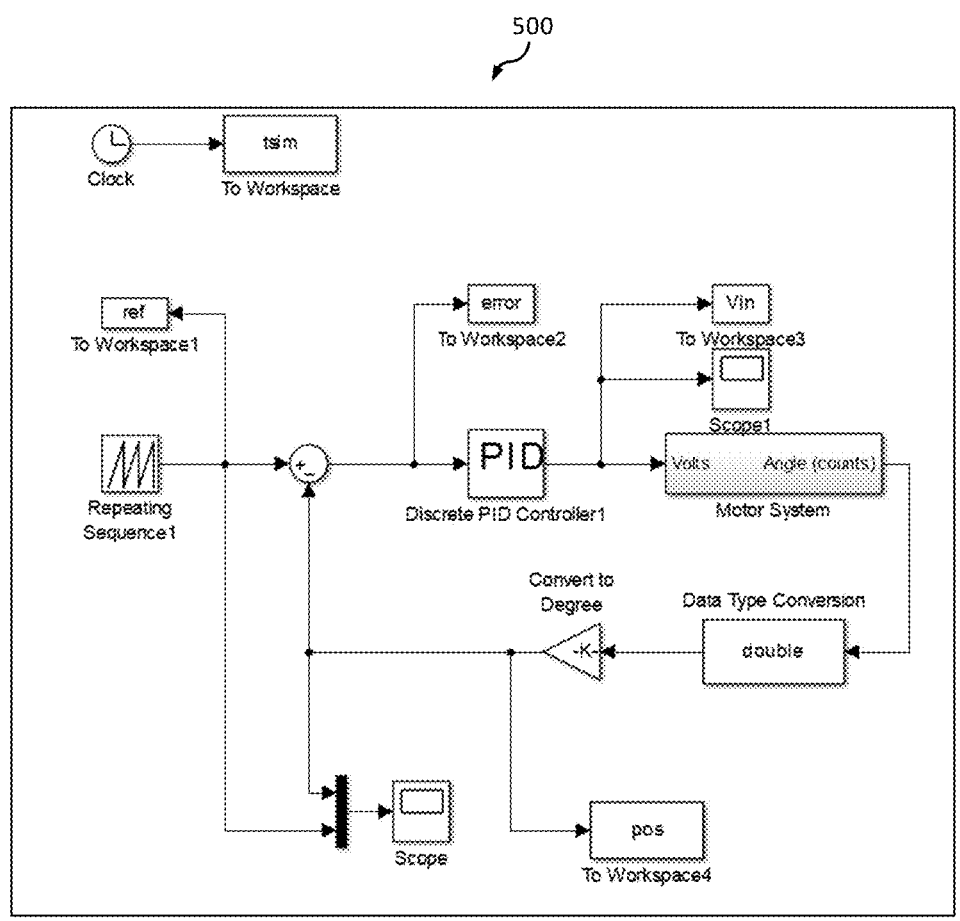
FIG. 5 is schematic illustrating a control system in accordance with one embodiment of the present invention.

In reference to FIG. 5, a Simulink diagram is shown to illustrate the system used to regulate the rotational velocity of a DC Motor by implementing PID controls and closed feedback loop. Different values like error, input voltage, velocity and others are saved to Workspace to process.

FIG. 10 B, a block diagram (1050) demonstrates one embodiment of the actuator and measuring system. The system is provided power (1052) which drives the motor (1054) in the direction determined by the directional switch (1056). The current drawn by the motor is measured (1060) by a current measuring system while the position of the motor is measured (1058) using a position measuring system. The data from the current measuring system (1060) and the position measuring system (1058) is captured by a data acquisition system or microprocessor (1062) and the result is displayed (1064).

FIG. 10C, a block diagram of the preferred embodiment (1070) of the actuator and measuring system shows DC power (1072) driving a DC motor (1074) in the direction determined by the directional switch (1076). The current drawn is measured by an ammeter (1080) while the position of the motor is measured by an encoder (1078). The data from the ammeter (1080) and encoder (1078) are captured by a data acquisition system or microprocessor (1082) and the result is displayed (1084).

Figure 11:
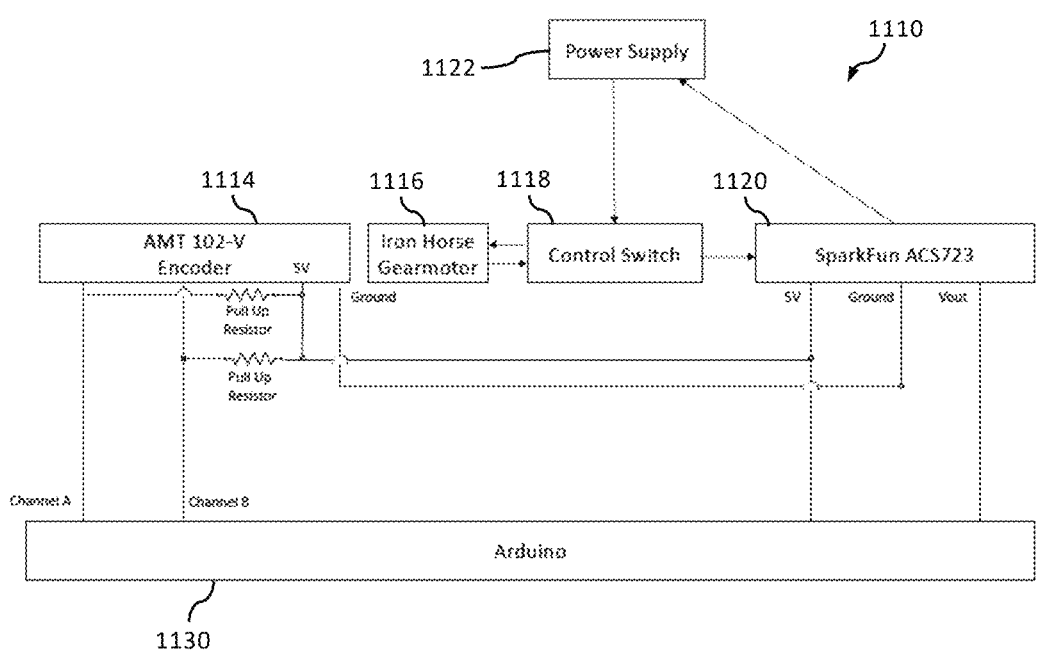
FIG. 11 illustrates a schematic of a control system in accordance with one embodiment of the present invention.

FIG. 11, in one embodiment, a DC power supply (1122) supplies power to a control switch (1118) which drives an Iron Horse Gearmotor (1116). The encoder (1114) measures position of the motor (1116). A SparkFun ACS723 (1120) circuit measures the current. Position and current are provided to the Arduino (1130) microprocessor.

While the present teachings have been described above in terms of specific embodiments, it is to be understood that they are not limited to those disclosed embodiments. Many modifications and other embodiments will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. A system for determining a force being generated by a patient at a plurality of intervals during a range of motion by the patient during a movement of the patient, the system comprising:
    a tether having a first end and a second end, the first end of the tether adapted to be biased by the patient during the range of motion by the patient during the movement of the patient so that the force generated by the patient is applied to the tether as a tension force during the range of motion;
    a motor fixed relative to a frame, the motor comprising a shaft having an axis of rotation, the tether being connected to the shaft so that when the force generated by the patient is applied to the tether during the range of motion by the patient during the movement of the patient the tether generates a patient torque about the shaft in a first direction about the axis of rotation of the shaft;
    a display;
    a data store;
    a controller in communication with the motor, the display, and the data store, a software executing on the controller to perform a plurality of actions on the controller, the plurality of actions comprising:
        controlling the motor to generate a motor torque in a second direction during the range of motion about the axis of rotation of the shaft, the second direction being opposite the first direction, when the force generated by the patient is applied to the tether during the range of motion by the patient during the movement of the patient;
        storing the motor torque in the data store at the plurality of intervals during the range of motion by the patient during the movement of the patient and storing a cumulative rotation of the shaft in the first direction at each of the intervals, the cumulative rotation in the first direction corresponding to a length of the tether unfurled from the shaft at each interval, and the motor torque corresponding to the force generated by the patient at each interval;
        generating a plot of the length of the tether unfurled from the shaft at each interval during the range of motion by the patient during the movement of the patient versus the force generated by the patient at each interval.

2. The system of claim 1, wherein the plurality of actions further comprises:
    controlling the motor torque in the second direction in proportion to the patient torque applied by the tether during the range of motion by the force generated by the patient during the range of motion so that the shaft of the motor has a constant rotational velocity in the first direction about the axis of rotation of the shaft.

3. The system of claim 2, wherein the plurality of actions further comprises:
    varying an electrical current supplied to the motor.

4. The system of claim 3, further comprising an interface in communication with the controller, the plurality of actions further comprising:
    receiving an indication via the interface regarding an exercise type associated with the range of motion.

5. The system of claim 2, wherein the plurality of actions further comprises:
associating the plot with a patient identifier.

6. The system of claim 5, wherein the plurality of actions further comprises:
generating a visual display simultaneously showing the plot of the length of the tether unfurled from the shaft at each interval versus the force generated by the patient at each interval and a second plot of a length of the tether unfurled from the shaft at each interval versus a force generated by the patient at each interval, the second plot being recorded for a different range of motion,
wherein the visual display enables a comparison between the plot and the second plot.

7. The system of claim 2, wherein the generated plot is configured to be shown on the display.

8. The system of claim 2, further comprising an encoder, wherein the encoder is configured to monitor the cumulative rotation of the shaft and determine a displacement of the tether, wherein the displacement correlates to the range of motion.

9. The system of claim 1, wherein the frame comprises a chair having a surface configured to support a portion of the patient.

10. The system of claim 9, further comprising a pulley configured to support the tether during the range of motion.

11. The system of claim 10, further comprising a gear being fixed on the shaft of the motor, wherein the tether is connected to the shaft via the gear.

12. The system of claim 11, wherein the motor is selectively fixed to the frame and the motor has an unlock mode and a lock mode, wherein in the unlock mode the motor is translatable relative to the frame and wherein in the lock mode the motor is fixed relative to the frame.

13. The system of claim 1, wherein the plurality of actions further comprises:
generating a second plot of a length of the tether unfurled from the shaft at each of the plurality of intervals versus a force generated by the patient at each interval, the second plot being recorded for a different range of motion recorded at a different time.

14. The system of claim 13, wherein the plot and the second plot represent data captured on separate days.

15. The system of claim 13, wherein the plurality of actions further comprises:
generating a visual display simultaneously showing the plot and the second plot,
wherein the visual display enables a comparison between the plot and the second plot.

16. A method for determining a force being generated by a patient at a plurality of intervals during a range of motion by the patient during a movement of the patient, the method comprising:
providing a tether having a first end and a second end, the first end of the tether adapted to be biased by the patient during the range of motion by the patient during the movement of the patient so that the force generated by the patient is applied to the tether as a tension force during the range of motion;
biasing the first end of the tether by the patient during the range of motion by the patient during the movement of the patient;
providing a motor fixed relative to a frame, the motor comprising a shaft having an axis of rotation, the tether being connected to the shaft so that when the force generated by the patient is applied to the tether during the range of motion by the patient during the movement of the patient the tether generates a patient torque about the shaft in a first direction about the axis of rotation of the shaft;
controlling the motor to generate a motor torque in a second direction during the range of motion about the axis of rotation of the shaft, the second direction being opposite the first direction, when the force generated by the patient is applied to the tether during the range of motion by the patient during the movement of the patient;
storing the motor torque in a data store at a plurality of intervals during the range of motion by the patient during the movement of the patient and storing a cumulative rotation of the shaft in the first direction at each of the intervals, the cumulative rotation in the first direction corresponding to a length of the tether unfurled from the shaft at each interval, and the motor torque corresponding to the force generated by the patient at each interval;
generating a plot of the length of the tether unfurled from the shaft at each interval during the range of motion by the patient during the movement of the patient versus the force generated by the patient at each interval.

17. The method of claim 16, further comprising the step of:
controlling the motor torque in the second direction in proportion to the patient torque applied by the tether during the range of motion by the force generated by the patient during the range of motion so that the shaft of the motor has a constant rotational velocity in the first direction about the axis of rotation of the shaft.

18. The method of claim 17, further comprising the step of:
storing the plot associated with a patient identifier.

19. The method of claim 16, wherein the step of controlling the motor to generate the motor torque comprises varying an electrical current supplied to the motor.

20. The method of claim 16 further comprising the steps of:
providing a gear fixed on the shaft of the motor, and connecting the tether to the shaft via the gear.

21. The method of claim 16, further comprising the step of:
receiving an indication regarding an exercise type associated with the range of motion.

22. The method of claim 16, further comprising the step of:
generating a display simultaneously showing the plot of the length of the tether unfurled from the shaft at each interval versus the force generated by the patient at each interval and a second plot of a length of the tether unfurled from the shaft at each interval versus a force generated by the patient at each interval, the second plot being recorded for a different range of motion.

23. The method of claim 16, further comprising the step of:
providing an encoder, wherein the encoder is configured to monitor the cumulative rotation of the shaft and determine a displacement of the tether, wherein the displacement correlates to the range of motion.

* * * * *